(12) United States Patent
Danenberg

(10) Patent No.: US 7,138,507 B2
(45) Date of Patent: Nov. 21, 2006

(54) METHOD OF DETERMINING A CHEMOTHERAPEUTIC REGIMEN BASED ON GLUTATHIONE-S TRANSFERASE PI EXPRESSION

(75) Inventor: Kathleen D. Danenberg, Altadena, CA (US)

(73) Assignee: Response Genetics, Inc., New York, NY (US)

( * ) Notice: Subject to any disclaimer, the term of this patent is extended or adjusted under 35 U.S.C. 154(b) by 179 days.

(21) Appl. No.: 10/654,575

(22) Filed: Sep. 4, 2003

(65) Prior Publication Data

US 2005/0019783 A1 Jan. 27, 2005

Related U.S. Application Data

(62) Division of application No. 09/879,986, filed on Jun. 14, 2001, now Pat. No. 6,686,155.

(51) Int. Cl.
C07H 21/02 (2006.01)
(52) U.S. Cl. ..................... 536/23.1; 435/91.2
(58) Field of Classification Search ............... 435/6, 435/91.2; 536/24.3
See application file for complete search history.

(56) References Cited

U.S. PATENT DOCUMENTS

| | | | |
|---|---|---|---|
| 4,830,969 A | 5/1989 | Holmes | 435/259 |
| 4,843,155 A | 6/1989 | Chomczynski | 536/27 |
| 5,128,247 A | 7/1992 | Koller | 435/91 |
| 5,204,241 A * | 4/1993 | Pero | 435/15 |
| 5,284,940 A | 2/1994 | Lin et al. | 536/25.4 |
| 5,346,994 A | 9/1994 | Chomczynski | 530/419 |
| 5,502,166 A | 3/1996 | Mishina | 530/350 |
| 5,620,852 A | 4/1997 | Lin et al. | 435/6 |
| 5,637,687 A | 6/1997 | Wiggins | 536/25.4 |
| 5,643,767 A | 7/1997 | Fischetti et al. | 435/91.3 |
| 5,654,179 A | 8/1997 | Lin | 435/91.2 |
| 5,672,696 A | 9/1997 | Wang et al. | 536/25.42 |
| 5,707,802 A | 1/1998 | Sandhu et al. | 435/6 |
| 5,728,822 A | 3/1998 | Macfarlane | 536/25.41 |
| 5,777,099 A | 7/1998 | Mehra | 536/25.42 |
| 5,942,389 A * | 8/1999 | Kirschling et al. | 435/366 |
| 5,945,515 A | 8/1999 | Chomczynski | 530/412 |
| 5,989,857 A | 11/1999 | Mundschenk | 435/69.1 |
| 6,010,700 A | 1/2000 | Richt | 424/186.1 |
| 6,043,354 A | 3/2000 | Hillebrand et al. | 536/25.42 |
| 6,136,605 A * | 10/2000 | Fahl et al. | 435/440 |
| 6,248,535 B1 | 6/2001 | Danenberg et al. | |

FOREIGN PATENT DOCUMENTS

| WO | WO 95/28489 A | 10/1995 |
|---|---|---|
| WO | WO 97/05248 | 2/1997 |
| WO | WO 97/35034 | 9/1997 |
| WO | WO 98/41648 | 9/1998 |
| WO | WO 01/46402 A1 | 6/2001 |
| WO | WO 02/44423 A2 | 6/2002 |

OTHER PUBLICATIONS

GenBank Accession Nos. U30897, U62589 May 9, 1997.*
Sequence Search Results US-10-654-575.*
Ali-Osman et al. "Molecular Cloning, Characterization, and Expression in *Escherichia coli* of Full-length cDNA of Three Human Glutathione S-Transferase Pi Gene Variants" The Journal of Biological Chemistry. Apr. 11, 1997. vol. 272 No. 15, pp. 10004-10012.*
Buck et al, "Design strategies and performance of custom DNA sequencing primers", Biotechniques (1999) 27:528-536.*
Stanta et al. (Methods in Mol. Biology (1998) 86:113-9).*
Hillier, L. et al., "The WashU-Merck EST project", Database EMBL 'Online! *European Molecular Biological Laboratory*; Jul. 27, 1995, XP002315145, Database accession No. H39177, abstract.
Gaoming, C. et al., "Quantitation of GST-PI MRNA Expression by Polymerase Chain Reaction", *Zhongguo Zhongliu Linchuang—Chinese Journal of Clinical Oncology*, vol. 25, 1998, pp. 858-861, XP008040058, abstract.
Ardalan, B., et al., "Thymidylate Synthase Gene Expression in Normal and Malignant Colorectal Tissues: Relation to in vivo Response and Survival," Proceedings of the American Association for Cancer Research, vol. 37, Abstract No. 1376 (Mar. 1996).
Ausubel, F.M., ed., *Current Protocols In Molecular Biology*, John Wiley & Sons, Inc., vol. 1.; Strauss, W. M., "Preparation of Genomic DNA from Mammalian Tissue," Unit 2.2, pp. 2.2.1-2.2.3 (1998).
Ausubel, F.M., ed., *Current Protocols In Molecular Biology*, John Wiley & Sons, Inc., vol. 1.; Richards, E., et al., "Preparation of Genomic DNA from Plant Tissue," Unit 2.3, pp. 2.3.1-2.3.7 (1994).
Ausubel, F.M., ed., *Current Protocols In Molecular Biology*, John Wiley & Sons, Inc., vol. 1.;Wilson, K., "Preparation of Genomic DNA from Bacteria," Unit 2.4, pp. 2.4.1-2.4.5 (1994).
Banerjee, S.K., et al, "Microwave-Based DNA Extraction from Paraffin-Embedded Tissue for PCR Amplification," BioTechniques, vol. 18, No. 5, pp. 768, 770, 772, 773 (1995).
Benhattar, J., et al., "p53 Mutations as a Possible Predictor of Response to Chemotherapy in Metastatic Colorectal Carcinomas," Int. J. Cancer (Pred. Oncol.), vol. 69, pp. 190-192 (1996).

(Continued)

*Primary Examiner*—Gary Benzion
*Assistant Examiner*—Christopher M Babic
(74) *Attorney, Agent, or Firm*—Kenyon & Kenyon

(57) ABSTRACT

The present invention relates to prognostic methods which are useful in medicine, particularly cancer chemotherapy. The object of the invention to provide a method for assessing GST-pi expression levels in fixed or fixed and paraffin embedded tissues and prognosticate the probable resistance or sensitivity of a patient's tumor to treatment with platinum-based therapies by examination of the amount of GST-pi mRNA in a patient's tumor cells and comparing it to a predetermined threshold expression level. More specifically, the invention provides to oligonucleotide primer pair GST-piand methods comprising their use for detecting levels of GST-pi mRNA.

3 Claims, 5 Drawing Sheets

OTHER PUBLICATIONS

Bresters, D., et al., "*Detection of Hepatitis C Viral RNA Sequences in Fresh and Paraffin-Embedded Liver Biopsy Specimens of Non-A, Non-B Hepatitis Patients*," J. Hepat., vol. 15, pp. 391-395 (1992).

Bresters, D., et al., "*The Duration of Fixation Influences the Yield of HCV cDNA-PCR Products from Formalin-Fixed, Paraffin-Embedded Liver Tissue*," J. Virol. Method, vol. 48, pp. 267-272 (1994).

Chirgwin, J., M., et al., "*Isolation of Biologically Active Ribonucleic Acid from Sources Enriched in Ribonuclease*," Biochemistry, vol. 18, No. 24, pp. 5294-5299 (1979).

Chomczynski, P., et al., "*Single-Step Method of RNA Isolation by Acid Guanidinium Thiocyanate-Phenol-Chloroform Extraction*," Analytical Biochemistry, vol. 162, pp. 156-159 (1987).

Chomczynski, P., "*A Reagent for the Single-Step Simultaneous Isolation of RNA, DNA and Proteins from Cell and Tissue Samples*," BioTechniques, vol. 15, No. 3, pp. 532-534, 536-537 (1993).

Coombs, N. J., et al., "*Opimisation of DNA and RNA Extraction from Archival Formalin-Fixed Tissue*," Nucl. Acids Research, vol. 27, No. 16, pp. i-iii (1999).

Dakhama, A., et al., "*Amplification of Human β-Actin Gene by the Reverse Transcripase-Polymerase Chain Reaction: Implications for Assessment of RNA from Formalin-Fixed, Paraffin-Embedded Material*," J. Histochem. and Cytochem., vol. 44, No. 10, pp. 1205-1207 (1996).

de Andrés, B., et al., "*Improved Method for mRNA Extraction from Paraffin-Embedded Tissues*," BioTechniques, vol. 18, No. 1, pp. 42-43 (1995).

Eads, C. A., et al., "*CpG Island Hypermethylation in Human Colorectal Tumors is Not Associated with DNA Methyltransferase Overexpression*," Cancer Research, vol. 59, pp. 2302-2306 (1999).

Edamoto, Y., et al., "*Hepatitis C and B Virus Infections in Hepatocellular Carcinoma*," CANCER, vol. 77, No. 9, pp. 1787-1791 (1996).

Finke, J., et al., "*An Improved Strategy and a Useful Housekeeping Gene for RNA Analysis from Formalin-Fixed, Paraffin-Embedded Tissues by PCR*," BioTechniques, vol. 14, No. 3, pp. 448-453 (1993).

Goldsworthy, S. M., et al., "*Effects of Fixation on RNA Extraction and Amplification from Laser Capture Microdissected Tissue*," Molecular Carcinogenesis, vol. 25, pp. 86-91 (1999).

Greer, C. E., et al., "*PCR Amplification from Paraffin-Embedded Tissues*," Am. J. Clin. Pathol., vol. No. 95, No. 2, pp. 117-124 (1991).

Gruber, A. D., et al., "*Detection of Bovine Viral Diarrhea Virus RNA in Formalin-Fixed, Paraffin-Embedded Brain Tissue by Nested Polymerase Chain Reaction*," J. Virol. Methods, vol. 43, pp. 309-319 (1993).

Guerrero, R.B., et al., "*Effects of Formalin Fixation and Prolonged Block Storage on Detection of Hepatitis C Virus RNA in Liver Tissue*," Diag. Molec. Path., vol. 6, No. 5, pp. 277-281 (1997).

Heid, C. A., et al., "*Real Time Quantitative PCR*," Genome Research, vol. 6, pp. 986-994 (1996).

Hodges, E., et al., "*Isolation of Nucleic Acid from Paraffin Embedded Tissue for PCR Amplification and Sequencing of TcR Vβ Genes*," Leuk. Research, vol. 19, No. 3, pp. 183-186 (1995).

Horie, N., et al., "*Functional Analysis and DNA Polymorphism of the Tandemly Repeated Sequences in the 5' terminal Regulatory Region of the Human Gene for Thymidylate Synthase*," Cell Structure and Function, vol. 20, No. 3, pp. 191-197 (1995).

Horikoshi, T., et al., "*Quantitation of Thymidylate Synthase, Dihydrofolate Reductase, and DT-Diaphorase Gene Expression in Human Tumors using the Polymerase Chain Reaction*," Cancer Res., vol. 52, pp. 108-116 (1992).

Hsuih, T. C. H., et al., "*Novel, Ligation-Dependent PCR Assay for Detection of Hepatitis C Virus in Serum*," J. Clin. Microbiol., vol. 34, No. 3, pp. 501-507 (1996).

Ichikawa, W., et al., "*Expression of Dihydropyrimidine Dehydrogenase (DPD) and Thymidylate Synthase (TS) mRNA in Primary Tumor Predicts the Anti-Tumor Effect in 5-Fluorouracil (FU Based Chemotherapy for Gastrointestinal (GI) Cancer*," Proceedings of the American Association for Cancer Research, vol. 42, Abstract No. 3326 (Mar. 2001).

Iwamoto, K. S., et al., "*Feasibility of Using Decades-Old Archival Tissues in Molecular Oncology/Epidmiology*," Am. J. Path., vol. 149, No. 2, pp. 399-406 (1996).

Jackman, A. L., et al., "*Thymidylate Synthetase Inhibitors: Experimental and Clinical Aspects*," Chapter 7 in Experimental and Clinical Progress in Cancer Chemotherapy, F.M. Muggia, ed., Martinus Nijhoff, Boston (1985), pp. 155-210.

Jiang, Y.-H., et al., "*A Rapid RT-PCR Method for Detection of Intact RNA in Formalin-Fixed Paraffin-Embedded Tissues*," Nucl. Acids. Res., vol. 23, No. 15, pp. 3071-3072 (1995).

Kawakami, K., et al., "*Polymorphic Tandem Repeats in the Thymidylate Synthase Gene is Associated with its Protein Expression in Human Gastrointestinal Cancers*," Proceedings of the American Society of Clinical Oncology, vol. 17, Abstract No. 1128 (May 1998).

Keyomarsi, K., et al., "*Mechanism of the Cytotoxic Synergism of Fluoropyrimidines and Folinic Acid in Mouse Leukemic Cells*," J. Biol. Chem., vol. 263, No. 28, pp. 14402-14409 (1988).

Kiyosawa, K., et al., "*Interrelationship of Blood Transfusion, Non-A, Non-B Hepatitis and Hepatocellular Carcinoma: Analysis of Detection of Antibody to Hepatitis C Virus*," Hepatology, vol. 12, No. 4, pp. 671-675 (1990).

Koopmans, M., et al., "*Optimization of Extraction and PCR Amplification of RNA Extracts from Paraffin-Embedded Tissue in Different Fixatives*," J. Virological Methods, vol. 43, pp. 189-204 (1993).

Leichman, C. G., et al., "*Quantitation of Intratumoral Thymidylate Synthase Expression Predicts for Disseminated Colorectal Cancer Response and Resistance to Protracted-Infusion Fluorouracil and Weekly Leucovorin*," J. Clinical Oncology, vol. 15, No. 10, pp. 3223-3229 (1997).

Lenz, H.-J., et al., "*p53 and Thymidylate Synthase Expression in Untreated Stage II Colon Cancer: Associations with Recurrence, Survival, and Site*," Clinical Cancer Research, vol. 4, pp. 1227-1234 (1998).

Lenz, H.-J., et al., "*Thymidylate Synthase mRNA Level in Adenocarcinoma of the Stomach: A Predictor for Primary Tumor Response and Overall Survival*," J. Clinical Oncology, vol. 14, No. 1, pp. 176-182 (1996).

Macfarlane, D. E., et al., "*Introduction to Isolating RNA*," in RNA Isolation and Characterization Protocols, R. Rapley and D. L. Manning, eds., Humana Press (Series: Methods in Molecular Biology™), Totowa, N. J. (1998), pp. 1-6.

Marsh, S., et al., "*Ethnic Variation in the Thymidylate Synthase Enhancer Region Polymorphism among Caucasian and Asian Populations*," Genomics, vol. 58, pp. 310-312 (1999).

Mies, C., "*A Simple, Rapid Method for Isolating RNA from Paraffin-embedded Tissues for Reverse Transcription-Polymerase Chain Reaction (RT-PCR)*," J. Histochemistry and Cytochemistry, vol. 42, No. 6, pp. 811-813 (1994).

Mizuno, T., et al., "*RNA from Decades-Old Archival Tissue Blocks for Retrospective Studies*," Diagnostic Molecular Pathology, vol. 7, No. 4, pp. 202-208 (1998).

Mukhopadhyay, T., et al., "*Isolation of Total RNA from Tissues or Cell Lines*," in RNA Isolation and Characterization Protocols, R. Rapley and D. L. Manning, eds., Humana Press (Series: Methods in Molecular Biology™), Totowa, N.J. (1998), pp. 55-59.

Park, Y. N., et al., "*Detection of Hepatitis C Virus RNA Using Ligation-Dependent Polymerase Chain Reaction in Formalin-Fixed, Paraffin-Embedded Liver Tissues*," American Journal of Pathology, vol. 149, No. 5, pp. 1485-1491 (1996).

Rupp, G. M., et al., "*Purification and Analysis of RNA from Paraffin-Embedded Tissues*," BioTechniques, vol. 6, No. 1, pp. 56-60 (1988).

Sambrook, J., et al., "*Isolation of High-Molecular-Weight DNA from Mammalian Cells*," in Molecular Cloning: A Laboratory Manual, $2^{nd}$ Ed., Cold Spring Harbor Laboratory Press (1989), pp. 9.14-9.23.

Sander, C. A., et al., "*p53 Mutation is Associated with Progression in Follicular Lymphomas*," Blood, vol. 82, No. 7, pp. 1994-2004 (1993).

Santos, A. C., et al., "*Simultaneous Extraction of RNA and DNA from Paraffin-Embedded Tissues*," Trends in Genetics, vol. 9, No. 7, pp. 231 (1993).

Soguero, C., et al., "*Detection of Hepatitis C Virus RNA in More Than 20-Year Old Paraffin-Embedded Liver Tissue*," Laboratory Investigation, vol. 79, No. 3, pp. 365-366 (1999).

Sorg, I., et al., "*Detection of Borna Disease Virus RNA in Formalin-Fixed, Paraffin-Embedded Brain Tissues by Nested PCR*," J. Clinical Microbiology, vol. 33, No. 4, pp. 821-823 (1995).

Spears, C. P., et al., "*In Vivo Kinetics by Thymidylate Synthetase Inhibition in 5-Fluorouracil-Sensitive and -Resistant Murine Colon Adenocarcinomas*," Cancer Research, vol. 42, pp. 450-456 (1982).

Stanta, G., et al., "*RNA Extracted from Paraffin-Embedded Human Tissues is Amenable to Analysis by PCR Amplification*," BioTechniques, vol. 11, No. 3, pp. 304-308 (3 pages) (1991).

G. Stanta, et al., "*RNA Quantitative Analysis from Fixed and Paraffin-Embedded Tissues*," Methods in Molecular Biology, vol. 86, pp. 113-119 (1998).

Swain, S. M., et al., "*Fluorouracil and High-Dose Leucovorin in Previously Treated Patients with Metastatic Breast Cancer*," J. Clinical Oncology, vol. 7, No. 7, pp. 890-899 (1989).

Wei, X., et al., "*Molecular Basis of the Human Dihydropyrimidine Dehydrogenase Deficiency and 5-Fluorouracil Toxicity*," J. Clinical Investigation, vol. 98, No. 3, pp. 610-615 (1996).

v. Weizsäcker, F., et al., "*A Simple and Rapid Method for the Detection of RNA in Formalin-Fixed, Paraffin-Embedded Tissues by PCR Amplification,*" Biochem. and Biophys. Research Comm., vol. 174, No. 1, pp. 176-180 (1991).

Arai, Tadashi; Yasuda, Yo; Takaya, Tadatake; Hayakawa, Kazuyoshi; Toshima, Satoshi; Shibuya, Chiken; Kashiki, Yoshitomo; Yoshimi, Naoki and Shibayama, Maroki. "*Immunohistochemical Expression of Glutathione Transferase-pi in Untreated Primary Non-Small-Cell Lung Cancer*." Cancer Detection and Prevention, 24(3): pp. 252-257 (2000).

Bai, Fen; Nakanishi, Yoichi; Kawasaki, Masayuki; Takayam, Koichi; Yatsunami, Jun; Pei, Xin Hai; Tsuruta, Nobuko; Wakamatsu, Kentaro; Hara, Nobuyuki. "*Immunohistochemical Expression of Glutathione S-Transferase-II Can Predict Chemotherapy Response in Patients with Nonsmall Cell Lung Carcinoma*." Amer. Cancer Society, pp. 416-421 (Apr. 19, 1999).

Boddy, Alan V. and Ratain, Mark J. "*Pharmacogenetics in Cancer Etiology and Chemotherapy[1]*." Clinical Cancer Research, vol. 3, pp. 1025-1030 (Jul. 1997).

Boku, Narikazu; Chin, Keisho; Hosokawa, Koichi; Ohtsu, Atsushi; Yoshida, Shigeaki; Yamao, Takekazu; Kondo, Hitoshi; Shirao, Kuniaki; Shimada, Yasuhiro; Saito, Daizo; Hasebe, Takahiro; Seki, Shigeki; Saito, Horoshi; and Johnston, Patrick G. "*Biological Markets as a Predictor for Response and Prognosis of Unresectable Gastric Cancer Patients Treated with 5-Fluorouracil and cis-Platinum[1]*." Clinical Cancer Research, vol. 4, pp. 1469-1474 (Jun. 1998).

Brockmöller, Jürgen; Cascorbi, Ingolf; Henning, Stefan; Meisel, Christian; and Roots, Ivan. "*Molecular Genetics of Cancer Susceptibility*." Pharmacology 2000, pp. 212-227.

Carmichael, James and Hickson, Ivan D. Keynote Address: "*Mechanisms of Cellular Resistance to Cytotoxic Drugs an X-Irradiation*." Intl. J of Raiation Oncol., vol. 20, pp. 197-202 (Feb. 1991).

Cazenave, Lorraine A.; Moscow, Jeffrey A.; Myers, Charles E.; and Cowan, Kenneth H. "*Glutathione S-transferase and Drug Resistance*." Drug Resistance in Cancer Therapy, pp. 171-187, Kluwer Academic Publishers, 1989.

Dabholkar, Meenakshi; Vionnet, Justine; Bostick-Bruton, Frieda; Uy, Jing jie; and Reed, Eddie. "*Messenger RNA Levels of XPAC and ERCC1 in Ovarian Cancer Tissue Correlate with Response to Platinum-based Chemotherapy*." J. of Clinical Investigations, Inc., vol. 94, pp. 703-708, Aug. 1994.

Davies, Stella M.; Robison, Leslie L.; Buckley, Jonathan D.; Tjoa, Tom; Woods, William G.; Radloff, Gretchen A.; Ross, Julie A.; and Perentesis, John P. "*Glutathione S-Transferase Polymorphisms and Outcome of Chemotherapy in Childhood Acute Myeloid Leukemia*." J of Clinical Oncology, vol. 19, No. 5, pp. 1279-1287, Mar. 1, 2001.

Dietel, M. "*Molecular Mechanism and Possibilities of Overcoming Drug Resistance in Gastrointestinam Tumors*." Recent Results in Cancer Research, vol. 142, pp. 89-101, 1996.

Djuric, Zora, Malviya, Vinay K.; Deppe, Gunter; Malone, Jr., John M.; McGunagle, Dawn L.; Heilbrun, Lance K.; Reading, Bruce A.; and Lawrence, William D. "*Detoxifying Enzymes in Human Ovarian Tissues: Comparison of Normal and Tumor Tissues and Effects of Chemotherapy*." J Cancer Research and Clinical Oncology, vol. 116, No. 4, pp. 379-383, 1990.

Fan, Kaichun; Fan, Daiming; Cheng, Liu Fang; and Li, Chunhali. "*Expression of Multidrug Resistance-related Markers in Gastric Cancer*." Intl. Journal of Cancer Research and Treatment, vol. 20, No. 6C, pp. 4809-4818, 2000.

Hida, Toyoaki; Kuwabara, Masaki; Ariyoshi, Yutaka; Takashi, Takashi; Sugiura; Hosoda, Kenji; Niitsu, Yoshiro and Ueda, Ryuzo. "*Serum Glutathione S-Transferase-II Level as a Tumor marker for Non-Small Cell Lung Cancer*." Cancer, vol. 73, No. 5, pp. 1377-1382, 1994.

Howells, Robert E.; Redman, Charles W.E.; Dhar, Kalyan K.; Sarhanis, Panos; Musgrove, Carylyn; Jones, Peter W.; Alldersea, Julie; Fryer, Anthony A.; Hoban, Paul R.; and Strange, Richard C. "*Association of Glutathione S-Transferase GSTM1 and GSTT1 Null Genotypes with Clinical Outcome in Epithelial Ovarian Cancer*." Clinical Cancer Research, vol. 4, No. 10, pp. 2439-2445, Oct. 1998.

Iyer, L. and Ratain, M.J. "*Clinical Oncology Update—Pharmacogenetics and Cancer Chemotherapy*." Euro J of Cancer, vol. 34, No. 10, pp. 1493-1499, Mar. 1, 1998.

Kelley, M. Kathleen; Engqvist-Goldstein, Asa; Montali, Julie A.; Wheatley, Jeffrey B.; Schmidt, Jr., Donald E.; and Kauvar, Lawrence M. "*Variability of Glutathione S-transferase Isoenzyme Patterns in Matched Normal and Cancer Human Breast Tissue*." Biochemical Journal, vol. 304, Pt. 3, pp. 843-848, 1994.

Linsenmeyer, M.E.; Jefferson, S.; Wolf, M.; Matthews, J.P.; Board, P.G.; and Woodcock, D.M. "*Levels of Expression of the mdr1 Gene and Glutathione S-Transferase Genes 2 and 3 and Response to Chemotherapy in Multiple Myeloma*." Br. J. Cancer, vol. 65, pp. 471-475, 1992.

Peters, W.H.M.; Roelofs, H.M.J.; van Putten, W.L.J.; Jansen, J.B. M.; Klijn, J.G.M. and Foekens, J.A. "*Response to adjuvant chemotherapy in primary breast cancer: no correlation with expression of glutathione S-transferases*." Br. J. Cancer, vol. 68, pp. 86-92, 1993.

Mayr, Doris; Pannekamp, Uwe; Baretton, Gustavo Bruno; Gropp, Martina; Meier, Werner; Flens, marcel Jan; Scheper, Rik; and Diebold, Joachim. "*Immunohistochemical Analysis of Drug Resistance-associated Proteins in Ovarian Carcinomas*." Pathology. Research Parctice, vol. 196, pp. 469-475, 2000.

Nakanishi, Yoichi; Kawasaki, Masayuki; Bai, Fen; Takayama, Koichi; Pei, Xin-Hai; Takano, Koichi; Inoue, Koji; Osaki, Sin-ichi; Hara, Nobuyuki; Kiyohara, Chikako. "*Expression of p53 and Glutathione S-Transferase-II Relates to Clinical Drug Resistance in Non-Small Cell Lung Cancer*." Oncology, vol. 57, pp. 318-323, 1999.

Niitsu, Y.; Takahashi, Y.; Ban, N.; Takayama, T.; Saito, T.; Katahira, T.; Umetsu, Y.; Nakajima, T.; Ohi, M.; Kuga, T.; Sakamaki, S.; Matsunaga, T.; Hirayama, Y.; Kuroda, H.; Homma, H.; Kato, J.; Kogawa, K. "*A proof of glutathione S-transferase-II-related multidrug resistance by transfer of antisense gene to cancer cells and sense gene to bone marrow stem cell*." Chemical-Biological Interationns, vol. 111-112, pp. 325-332, 1998.

Nishimura, Toshiro; Newkirk, Kenneth; Sessions, Roy B.; Andrews, Paul A.; Trock, Bruce J.; Rasmussen, Audrey A.; Montgomery, Elizabeth A.; Bischoff, Elizabeth K.; and Cullen, Kevin J. "*Immunohistochemical Staining for Glutathione S-Transferase Predicts Response to Platinum-based Chemotherapy in Head and Neck Cancer*." Clinical Cancer Research, vol. 2, pp. 1859-1865, 1996.

Nitsu, Yoshiro; Takahashi, Yasuo; Saito, Tadanori; Hirata, Yasuji; Arisato, Nobuko; Maruyama, Hiroshi; Kohgo, Yutaka; and Listowsky, Irving. "*Serum Glutathione-S-Transferase-II as a Tumor Marker for Gastrointestinal Malignancies*." Cancer, vol. 63, pp. 317-323, 1989.

Nishiyama, Masahiko; Suzuki, Katsuyuki; and Kurisu, Kaoru. "*Molecular Targeting of Mitomycin C Chemotherapy*." Int. J. Cancer, vol. 72, pp. 649-656, 1997.

Nutt, Catherine L.; Noble, Mark; Chambers, Ann F.; and Cairncross, J. Greggory. "*Differential Expression of Drug Resistance Genes and Chemosensitivity in Glial Cell Lineages Correlate with Differential Response to Oligodendrogliomas and Astrocytomas to Chemotherapy." Cancer Research, vol. 60, No. 17, pp. 4812-4818, Sep. 1, 2000.

Oakley, Aaron J.; Rossjohn, Jamie; Bello, Mario Lo; Caccuri, Anna Maria; Federici, Giorgio; and Parker, Michael W. "The Three-Dimensional Structure of Human Pi Class Glutathione Transferase P1-1 in Complex with the Inhibitor Ethacrynic Acid and Its Glutathione." Biochemistry, vol. 36, pp. 576-585, 1997.

Kim, W.J.; Kakehi, Y.; Wu, W.J.; Fukumoto, M.; and Yoshida, O. "Expression of multidrug resistance-related genes (mdrl, MRP, GST-II and DNA topoisomerase II) in urothelial cancers." Br. J. of Urology, Vo. 78, No. 3, Sep. 1996.

Schisselbauer, John C.; Hogan, W. Michael; Buetow, Kenneth H.; and Tew, Kenneth D. "Heterogeneity of glutathione S-transferase enzyme and gene expression in ovarian carcinoma." Pharmacogenetics, vol. 2, No. 2, pp. 62-72, Apr. 1992.

Sheehan, D. and Meade, G. "Chemical modulation of chemotherapy resistance in cultered oesophageal carcinoma cells." Biochemical Society, vol. 28, pt. 2, pp. 27-32, 2000.

Stanulla, Martin; Schrappe, Martin, Brechlin, Annette Müller; Zimmermann, Martin; and Welte, Karl. "Polymorphisms within glutathione S-transferase genes (GSTM1, GSTT1, GSTP1) and risk of relapse in childhood B-cell precursor acute lymphoblastic leukemia: a case-control study." Blood, vol. 95, No. 4, pp. 1222-1228, Feb. 2000.

Tominga, Kazumari; Arakawa, Tetsu; Imano, Motohiro; Kato, Michio; Hamaguchi, Yuko; Watanabe, Toshio; Takaishi, Osamu; Fujiwara, Yashiro; Fukuda, Takashi; Higuchi, Kazuhide; Osugi, Harushi; Chono, Shinji; Kuroki, Tetsuo. "Complete Regression of Recurrent Esophageal Carcinoma With Reduced Expression of Glutathione S-Transferase-II by Treatment With Continuous Infusion of 5-Fluorouracil and Low-Dose Cisplatin Infusion." Am. J. of Gastroenterology, vol. 94, No. 6, pp. 1664-1669, 1999.

van der Zee, Ate G.J.; Hollema, Harry; Suurmeijer, Albrt J.H.; Krans, Mindert; Sluiter, Wim J.; Willemse, Pax H.B.; Aalders, Jan G.; and de Vries, Elisabeth G.E. "Value of P-Glycoprotein, Glutathione S-Transferase pi, c-erb B-2, and p53 as Prognostic Factors in Ovarian Carcinomas." J. of Clinical Oncology, vol. 13, No. 1, pp. 70-78, Jan. 1995.

Waxman, David J. "Glutathione S-Transferases: Role in Alkylating Agent Resistance and Possible Target for Modulation Chemotherapy—A Review." Cancer Review, vol. 50, pp. 6449-6454, Oct. 15, 1990.

Redmond, Shelagh, M.S.; Joncourt, Franziska; Buser, Kathi; Ziemiecki, Andrew; Altermatt; Hns-Jörg; Fey, Martin; Margison, Geoff; and Cerny, Thomas. "Assessment of P-Glycoprotein, Glutathione-based Detoxifying Enzymes and $O^6$-Alkylguanine-DNA Alkyltransferase as Potential Indicators of Constitutive Drug Resistance in Human Colorectal Tumors." Cancer Research, vol. 51, pp. 2092-2097, Apr. 15, 1997.

Shiga, Hideaki; Heath, Elizabeth I.; Rasmussen, Audrey A.; Trock, Bruce; Johnston, patrick G.; Forastiere, Arlene A.; Langmacher, Miles; Baylor, Alfred; Lee, Michele; and Cullen, Kevin J. "Prognostic Value of p53, Glutathione S-Transferase II, and Thymidylate Synthase for Neoadjuvant Cisplatin-based Chemotherapy in Head and Neck Cancer." Clinical Cancer Research, vol. 5, pp. 4097-4104, Dec. 1999.

Harpole, David H., Jr.; Moore, Mary-Beth; Herndon, James E., II; Aloia, Thomas; D;Amico, Thomas A.; Sporn, Thomas; Parr, Allyson; Linoila, Iiona; and Allegra, Carmen. "The Prognostic Value of Molecular Marker Analysis in Patients Treated with Trimodality Therapy for Esophageal Cancer." Clinical Cancer Research, vol. 7, p. 562-569, Mar. 2001.

Tiffoli, G.; Frustaci, S.; Tumiotto, L.; Talamini, R.; Gherlinzoni, F.; Picci, P.; and Boiocchi, M. "Expression of MDR1 and GST-II in human soft tissue sarcomas: Relation to drug resistance and biological aggressiveness." Annals of Oncology, vol. 3, pp. 63-69, 1992.

Welters, MJP; Fichtinger-Schepman, AMJ; Baan, RA; Flens, MJ; Scheper, RJ; and Braakhuis, BJM. "Role of glutathione, glutathione S-transferases and multidrug resistance-related proteins in cisplatin sensitivity of head and neck cancer cell lines." Br. J. of Cancer, vol. 77, Pt. 4, pp. 556-561, 1998.

Uozaki, H.; Horiuchi, H.; Ishida, T.; Iijima, T.; Imamura, T.; Machinami, R. "Overexpression of Resistance-Related Proteins (Metallothioneins, Glutathione-S-Transferase II, Heat Shock Protein 27, and Lung Resistance-Related Protein) in Osteosarcoma—Relationship with Poor Prognosis" Amer. Cancer Assn., Presentation, Oct. 12, 1996.

Farrugia, D.; Cunningham, D.; Danenberg, P.; Danenberg, K.; Metzger, R.; Mitchell, F.; MacVicar, D.; McCarthy, K.; Aheme, G.W.; Norman, A.; and Jackman, A.L. "A pharmacodynamic (PD) study of the thymidylate synthase (TS) inhibitor Toumdex™", Proceedings, 88th Annual Meeting of the American Association for Cancer Research, vol. 38, Mar. 1997.

Miyauchi, et al., "Further study of hepatitis C virus RNA detection in formalin -fixed, paraffin -embedded liver tissues by ligation-dependent polymerase chain reaction" Pathology International 1998:48: 428-432.

G. Stanta, et al., *RNA Extraction from Formalin-Fixed and Paraffin-Embedded Tissues*, Methods in Molecular Biology (1998) vol. 86, pp. 23-26.

* cited by examiner

Association between survival and GST-$\pi$ relative mRNA expression in patients with esophagocardiac adenocarcinoma treated with 5-FU and cisplatin. Patients with GST-$\pi$ values above the median value had a survival advantage compared to those with patients with values below the median. Censored values are denoted by a tick.

Survival analysis confined to patients with TNM Stage II esophagocardiac adenocarcinoma.

Survival analysis confined to patients with Stage II esophagocardiac adenocarcinoma.

| | Sample | From "Test" Reaction | | | From "Calibration" Reaction | | | | Uncorrected Gene Expression (UGE) $2^{-\Delta C_T}/2^{-\Delta C_T}$ | Published GSTP1 Values | Derivation of $K_{GSTP1}$ (Avg. K) | | Relative GSTP1 exp. |
|---|---|---|---|---|---|---|---|---|---|---|---|---|---|
| | | $C_T$ GSTP1 | $C_T$ β-ACTIN | $\Delta C_T$ | $2^{-\Delta C_T}$ | $C_T$ GSTP1 | $C_T$ β-ACTIN | $\Delta C_T$ | $2^{-\Delta C_T}$ | | | K | $K_{GSTP1}$ |  |
| Experimental | Unknown 1 | 27.87 | 20.57 | 4.99 | 0.0314674 | – | – | – | – | 0.15 | – | | $7.28 \times 10^{-3}$ | $1.10 \times 10^{-3}$ |
| | Unknown 2 | 24.32 | 19.91 | 2.2 | 0.2176376 | – | – | – | – | 1.05 | – | | $7.28 \times 10^{-3}$ | $7.65 \times 10^{-3}$ |
| | Calib. RNA | – | – | – | – | 21.43 | 19.16 | 2.27 | 0.2073299 | 0.207/0.207=1 | | | | – |
| From Published Data | 14-1 | 30.55 | 25.5 | 5.05 | 0.0301855 | – | – | – | – | 0.18 | $1.6 \times 10^{-3}$ | $9.05 \times 10^{-3}$ | $7.28 \times 10^{-3}$ | – |
| | 14-5 | 29.41 | 25.7 | 3.71 | 0.076415 | – | – | – | – | 0.45 | $2.91 \times 10^{-3}$ | $6.5 \times 10^{-3}$ | $7.28 \times 10^{-3}$ | – |
| | 14-8 | 31.41 | 27.1 | 4.31 | 0.0504151 | – | – | – | – | 0.31 | $2.91 \times 10^{-3}$ | $6.95 \times 10^{-3}$ | $7.28 \times 10^{-3}$ | – |
| | 13-24 | 30.16 | 25.42 | 4.74 | 0.0374212 | – | – | – | – | 0.22 | $1.45 \times 10^{-3}$ | $6.62 \times 10^{-3}$ | $7.28 \times 10^{-3}$ | – |
| | 13-25 | 29.27 | 25.5 | 3.77 | 0.0733022 | – | – | – | – | 0.43 | $3.12 \times 10^{-3}$ | $7.27 \times 10^{-3}$ | $7.28 \times 10^{-3}$ | – |
| | Calib. RNA | – | – | – | – | 26.09 | 23.54 | 2.55 | 0.170755 | 0.1707/0.1707=1 | | | | |

FIG. 4 CHART ILLUSTRATING HOW TO CALCULATE GSTP1 EXPRESSION RELATIVE TO AN INTERNAL CONTROL GENE

The primers and probe used

Forward primer: GST-F [24 bp, 59 C]:
CCTGTACCAGTCCAATACCATCCT,                    (SEQ ID NO: 1)
Reverse primer: GST-R [20 bp, 59 C]:
TCCTGCTGGTCCTTCCCATA                         (SEQ ID NO: 2)
TaqMan probe: GST-219T [20 bp, 69 C]:
TCACCTGGGCCGCACCCTTG                         (SEQ ID NO: 3)
Amplicon: 72 bp β-Actin TaqMan® probe:
ACCACCACGG CCGAGCGG                          (SEQ ID NO: 4)

β-Actin-592F
TGAGCGCGGC TACAGCTT                          (SEQ ID NO: 5)

β-Actin-651R
TCCTTAATGT CACGCACGAT                        (SEQ ID NO: 6)

FIG.5

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
cctgtaccag tccaatacca tcct                                          24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tcctgctggt ccttcccata                                               20

<210> SEQ ID NO 3
<211> LENGTH: 20
<212> TYPE: DNA
<213> ORGANISM: Artificial Sequence
<220> FEATURE:
<223> OTHER INFORMATION: Probe

<400> SEQUENCE: 3

```
tcacctgggc cgcacccttg                                               20

<210> SEQ ID NO 4
<211> LENGTH: 18
<212> TYPE: DNA
<213> ORGANISM: Artificial Sequence
<220> FEATURE:
<223> OTHER INFORMATION: Probe

<400> SEQUENCE: 4
accaccacgg ccgagcgg                                                 18

<210> SEQ ID NO 5
<211> LENGTH: 18
<212> TYPE: DNA
<213> ORGANISM: Artificial Sequence
<220> FEATURE:
<223> OTHER INFORMATION: Probe

<400> SEQUENCE: 5
tgagcgcggc tacagctt                                                 18

<210> SEQ ID NO 6
<211> LENGTH: 20
<212> TYPE: DNA
<213> ORGANISM: Artificial Sequence
<220> FEATURE:
<223> OTHER INFORMATION: Probe

<400> SEQUENCE: 6
tccttaatgt cacgcacgat                                               20
```

METHOD OF DETERMINING A CHEMOTHERAPEUTIC REGIMEN BASED ON GLUTATHIONE-S TRANSFERASE PI EXPRESSION

CROSS REFERENCE TO RELATED APPLICATION

This application is a divisional application of patent application Ser. No. 09/879,986 filed Jun. 14, 2001, now U.S. Pat. No. 6,686,155, which is incorporated herein in its entirety by reference thereto.

FIELD OF THE INVENTION

The present invention relates to prognostic methods which are useful in medicine, particularly cancer chemotherapy. More particularly, the invention relates to assessment of tumor cell gene expression in a patient. The resistance of tumor cells to chemotherapeutic agents that target DNA, especially agents that damage DNA in the manner of platinating agents is assayed by examining the mRNA expressed from genes involved in DNA repair in humans.

BACKGROUND OF THE INVENTION

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor. When a tumor is found, the clinical objective is to destroy malignant cells selectively while mitigating any harm caused to normal cells in the individual undergoing treatment.

Chemotherapy is based on the use of drugs that are selectively toxic (cytotoxic) to cancer cells. Several general classes of chemotherapeutic drugs have been developed, including drugs that interfere with nucleic acid synthesis, protein synthesis, and other vital metabolic processes. These generally are referred to as antimetabolite drugs. Other classes of chemotherapeutic drugs inflict damage on cellular DNA. Drugs of these classes generally are referred to as genotoxic. Susceptibility of an individual neoplasm to a desired chemotherapeutic drug or combination of drugs often, however, can be accurately assessed only after a trial period of treatment. The time invested in an unsuccessful trial period poses a significant risk in the clinical management of aggressive malignancies.

The repair of damage to cellular DNA is an important biological process carried out by a cell's enzymatic DNA repair machinery. Unrepaired lesions in a cell's genome can impede DNA replication, impair the replication fidelity of newly synthesized DNA and/or hinder the expression of genes needed for cell survival. Thus, genotoxic drugs generally are considered more toxic to actively dividing cells that engage in DNA synthesis than to quiescent, nondividing cells. Normal cells of many body tissues are quiescent and commit infrequently to re-enter the cell cycle and divide. Greater time between rounds of cell division generally is afforded for the repair of DNA damage in normal cells inflicted by chemotherapeutic genotoxins. As a result, some selectivity is achieved for the killing of cancer cells. Many treatment regimens reflect attempts to improve selectivity for cancer cells by coadministering chemotherapeutic drugs belonging to two or more of these general classes.

Because effective chemotherapy in solid tumors usually requires a combination of agents, the identification and quantification of determinants of resistance or sensitivity to each single drug has become an important tool to design individual combination chemotherapy.

Two widely used genotoxic anticancer drugs that have been shown to damage cellular DNA are cisplatin (DDP) and carboplatin. Cisplatin and/or carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. Cisplatin in combination with other agents is currently preferred for the management of testicular carcinoma, and in many instances produces a lasting remission. (Loehrer et al.,1984,100 Ann. Int. Med. 704). Cisplatin (DDP) disrupts DNA structure through formation of intrastrand adducts. Resistance to platinum agents such as DDP has been attributed to enhanced tolerance to platinum adducts, decreased drug accumulation, or enhanced DNA repair. Although resistance to DDP is multifactoral, alterations in DNA repair mechanisms probably play a significant role.

The glutathione-S-transferase (GST) family of proteins is involved in detoxification of cytotoxic drugs. By catalyzing the conjugation of toxic and carcinogenic electrophilic molecules with glutathione the GST enzymes protect cellular macromolecules from damage (Boyer et al., Preparation, characterization and properties of glutathione S-transferases. In: Zakim D, Vessey D (eds.) Biochemical Pharmacology and Toxicology. New York, N.Y.: John Wiley and Sons, 1985.). A certain isomeric type of these proteins, the glutathione S-transferase Pi (GST-pi, also to be interchangeably refered to as GSTP1 or GST-π herein) is widely expressed in human epithelial tissues and has been demonstrated to be over-expressed in several tumors (Terrier et al., Am J Pathol 1990; 137: 845–853; Moscow et al., Cancer Res 1989; 49: 1422–1428). Increased GST-pi levels have been found in drug resistant tumors, although the exact mechanism remains unclear (Tsuchida et al., Crit Rev Biochem Mol Biol 1992; 27: 337–384). Previous studies have suggested that low expression of GST protein (not mRNA) is associated with response to platinum-based chemotherapy (Nishimura et al., Cancer. Clin Cancer Res 1996; 2:1859–1865; Tominaga, et al., Am. J. Gastro. 94:1664–1668, 1999; Kase, et al., Acta Cytologia. 42: 1397–1402, 1998). However, these studies did not measure quantitative gene expression, but used a semi-quantitative immunohistochemical staining method to measure protein levels. However, quantitative GST-pi gene expression measurements are needed to achieve a very effective prognostication.

Most pathological samples are routinely fixed and paraffin-embedded (FPE) to allow for histological analysis and subsequent archival storage. Thus, most biopsy tissue samples are not useful for analysis of gene expression because such studies require a high integrity of RNA so that an accurate measure of gene expression can be made. Currently, gene expression levels can be only qualitatively monitored in such fixed and embedded samples by using immunohistochemical staining to monitor protein expression levels.

Until now, quantitative gene expression studies including those of GST-pi expression have been limited to reverse transcriptase polymerase chain reaction (RT-PCR) amplification of RNA from fresh or frozen tissue.

The use of frozen tissue by health care professionals poses substantial inconveniences. Rapid biopsy delivery to avoid tissue and subsequent mRNA degradation is the primary concern when planning any RNA-based quantitative genetic marker assay. The health care professional performing the biopsy, must hastily deliver the tissue sample to a facility equipped to perform an RNA extraction protocol immediately upon tissue sample receipt. If no such facility is available, the clinician must promptly freeze the sample in order to prevent mRNA degradation. In order for the diagnostic facility to perform a useful RNA extraction protocol prior to tissue and RNA degradation, the tissue sample must remain frozen until it reaches the diagnostic facility, however far away that may be. Maintenance of frozen tissue integrity during transport using specialized couriers equipped with liquid nitrogen and dry ice, comes only at a great expense.

Routine biopsies generally comprise a heterogenous mix of stromal and tumorous tissue. Unlike with fresh or frozen tissue, FPE biopsy tissue samples are readily microdissected and separated into stromal and tumor tissue and therefore, offer an advantage over the use of fresh or frozen tissue. However, isolation of RNA from fixed tissue, and especially fixed and paraffin embedded tissue, results in highly degraded RNA, which is generally not applicable to gene expression studies.

A number of techniques exist for the purification of RNA from biological samples, but none is reliable for isolation of RNA from FPE samples. For example, Chomczynski (U.S. Pat. No. 5,346,994) describes a method for purifying RNA from tissues based on a liquid phase separation using phenol and guanidine isothiocyanate. A biological sample is homogenized in an aqueous solution of phenol and guanidine isothiocyanate and the homogenate thereafter mixed with chloroform. Following centrifugation, the homogenate separates into an organic phase, an interphase and an aqueous phase. Proteins are sequestered in the organic phase, DNA in the interphase, and RNA in the aqueous phase. RNA can be precipitated from the aqueous phase. Unfortunately, this method is not applicable to fixed and paraffin-embedded (FPE) tissue samples.

Other known techniques for isolating RNA typically utilize either guanidine salts or phenol extraction, as described for example in Sambrook, J. et al., (1989) at pp. 7.3–7.24, and in Ausubel, F. M. et al., (1994) at pp. 4.0.3–4.4.7. Again, none of the known methods provides reproducible quantitative results in the isolation of RNA from paraffin-embedded tissue samples.

Techniques for the isolation of RNA from paraffin-embedded tissues are thus particularly needed for the study of gene expression in tumor tissues, since expression levels of certain receptors or enzymes can be used to determine the likelihood of success of a particular treatment.

There is a need for a method of quantifying GST-pi mRNA from paraffinized tissue in order to provide an early prognosis for proposed genotoxic cancer therapies. As a result, there has been a concerted yet unsuccessful effort in the art to obtain a quantification of GST-pi expression in fixed and paraffinized (FPE) tissue. Accordingly, it is the object of the invention to provide a method for assessing GST-pi levels in tissues fixed and paraffin-embedded (FPE) and prognosticate the probable resistance of a patient's tumor to treatment with DNA damaging agents, creating the type of lesions in DNA that are created by DNA platinating agents, by examination of the amount of GST-pi mRNA in a patient's tumor cells and comparing it to a predetermined threshold expression level.

SUMMARY OF THE INVENTION

In one aspect of the invention there is provided a method for assessing levels of expression of GST-pi mRNA obtained from fixed and paraffin-embedded (FPE) fixed and paraffin-embedded (FPE) tumor cells.

In another aspect of the invention there is provided a method of quantifying the amount of GST-pi mRNA expression relative to an internal control from a fixed and paraffin-embedded (FPE) tissue sample. This method includes isolation of total mRNA from said sample and determining the quantity of GST-pi mRNA relative to the quantity of an internal control gene's mRNA.

In an embodiment of this aspect of the invention, there are provided oligonucleotide primers having the sequence of GST-F (SEQ ID NO: 1) or GST-R (SEQ ID NO:2) and sequences substantially identical thereto. The invention also provides for oligonucleotide primers having a sequence that hybridizes to SEQ ID NO: 1 or SEQ ID NO:2 or their complements under stringent conditions.

In yet another aspect of the invention there is provided a method for determining a chemotherapeutic regimen for a patient, comprising isolating RNA from a fixed and paraffin-embedded (FPE) tumor sample; determining a gene expression level of GST-pi in the sample; comparing the GST-pi gene expression levels in the sample with a predetermined threshold level for the GST-pi gene; and determining a chemotherapeutic regimen based on results of the comparison of the GST-pi gene expression level with the predetermined threshold level.

The invention further relates to a method of normalizing the uncorrected gene expression (UGE) of GST-pi relative to an internal control gene in a tissue sample analyzed using TaqMan® technology to known GST-pi expression levels relative to an internal control from samples analyzed by pre-TaqMan® technology.

BRIEF DESCRIPTION OF THE DRAWINGS

FIG. 4 is a chart illustrating how to calculate GST-pi expression relative to an internal control gene. The chart contains data obtained with two test samples, (unknowns 1 and 2), and illustrates how to determine the uncorrected gene expression data (UGE). The chart also illustrates how to normalize UGE generated by the TaqMan® instrument with known relative GST-pi values determined by pre-TaqMan® technology. This is accomplished by multiplying UGE to a correction factor $K_{GST-pi}$. The internal control gene in the figure is β-actin and the calibrator RNA is Human Liver Total RNA (Stratagene, Cat. #735017).

FIG. 5 shows the oligonucleotide primers used in the present invention.

DETAILED DESCRIPTION OF THE INVENTION

Figure 1:
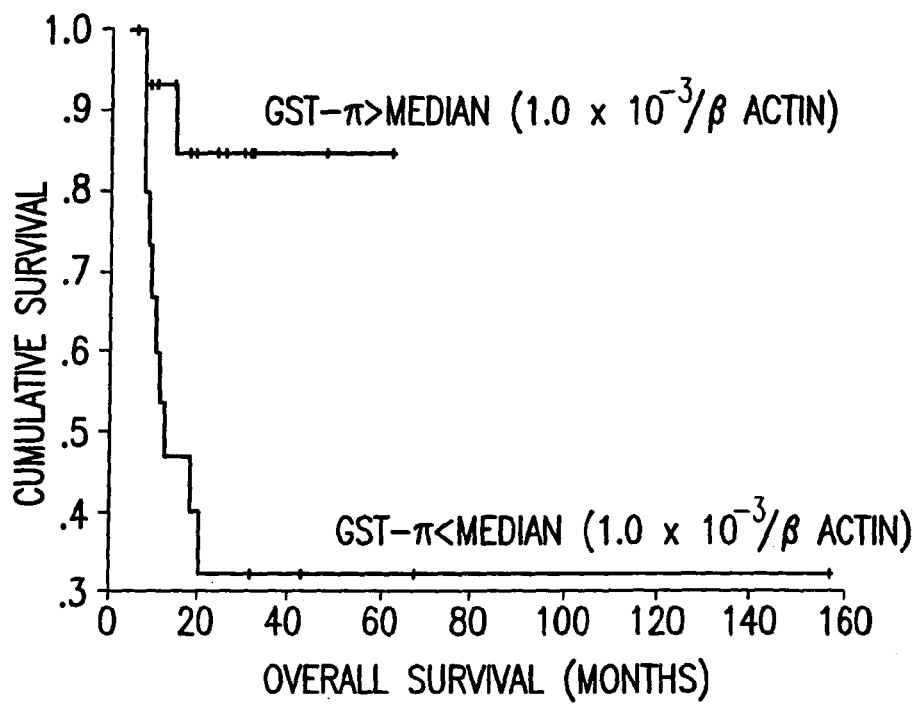
FIG. 1 shows and association between survival and GST-pi corrected relative mRNA expression in patients with esophagocardiac adenocarcinoma treated with 5-FU and cisplatin. Patients with GST-pi values above the median/threshold value had a survival advantage compared to those with patients with values below the median/threshold. Censored values are denoted by a tick.

The present invention resides in part in the finding that the amount of GST-pi mRNA is correlated with increased sensitivity to DNA platinating agents. Tumors expressing high levels of GST-pi mRNA are considered likely to be sensitive to platinum-based chemotherapy. Conversely, those tumors expressing low amounts of GST-pi mRNA are likely to be insensitive to platinum-based chemotherapy. A patient's relative expression of tumor GST-pi mRNA is judged by comparing it to a predetermined threshold expression level. Such sensitivity or lack thereof to DNA platinating agents is determined by a patient's survivability.

The invention relates to a method of quantifying the amount of GST-pi mRNA expression in fixed and paraffin-embedded (FPE) tissue relative to gene expression of an internal control. The present inventors have developed oligonucleotide primers that allow accurate assessment of GST-pi expression in tissues that have been fixed and embedded. The invention oligonucleotide primers, GST-F (SEQ ID NO: 1), GST-R (SEQ ID NO: 2), or oligonucleotide primers substantially identical thereto, preferably are used together with RNA extracted from fixed and paraffin embedded (FPE) tumor samples. This measurement of GST-pi gene expression may then be used for prognosis of platinum-based chemotherapy.

This embodiment of the invention involves first, a method for reliable extraction of RNA from an FPE sample and second, determination of the content of GST-pi mRNA in the sample by using a pair of oligonucleotide primers, preferably oligonucleotide primer pair GST-F (SEQ ID NO: 1) and GST-R (SEQ ID NO: 2), or oligonucleotides substantially identical thereto, for carrying out reverse transcriptase polymerase chain reaction. RNA is extracted from the FPE cells by any of the methods for mRNA isolation from such samples as described in U.S. patent application Ser. No. 09/469,338, filed Dec. 20, 1999, now U.S. Pat. No. 6,248,535, and is hereby incorporated by reference in its entirety.

The present method can be applied to any type of tissue from a patient. For examination of sensitivity of tumor tissue, it is preferable to examine the tumor tissue. In a preferred embodiment, a portion of normal tissue from the patient from which the tumor is obtained, is also examined.

The methods of the present invention can be applied over a wide range of tumor types. This allows for the preparation of individual "tumor expression profiles" whereby expression levels of GST-pi are determined in individual patient samples and response to various chemotherapeutics is predicted. Preferably, the methods of the invention are applied to solid tumors, most preferably esophogocardiac tumors. For application of some embodiments of the invention to particular tumor types, it is preferable to confirm the relationship of GST-pi gene expression levels to clinical resistance by compiling a data-set that enables correlation of a particular GST-pi expression and clinical resistance to platinum-based chemotherapy.

A "predetermined threshold level", as defined herein, is a level of GST-pi expression above which it has been found that tumors are likely to be sensitive to a platinum-based chemotherapeutic regimen. Expression levels below this threshold level are likely to be found in tumors insensitive to platinum-based chemotherapeutic regimen. The range of corrected relative expression of GST-pi, expressed as a ratio of GST-pi: β-actin, among tumors responding to a platinum-based chemotherapeutic regimen is more than about $1.0 \times 10^{-3}$. Tumors that do not respond to a platinum-based chemotherapeutic regimen have relative expression of GST-pi: β-actin ratio below about $1.0 \times 10^{-3}$. FIG. 1. However, the present invention is not limited to the use of β-actin as an internal control gene.

In performing the method of this embodiment of the present invention, tumor cells are preferably isolated from the patient. Solid or lymphoid tumors or portions thereof are surgically resected from the patient or obtained by routine biopsy. RNA isolated from frozen or fresh samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

However, tissue obtained from the patient after biopsy is often fixed, usually by formalin (formaldehyde) or gluteraldehyde, for example, or by alcohol immersion. Fixed biological samples are often dehydrated and embedded in paraffin or other solid supports known to those of skill in the art. Non-embedded, fixed tissue may also be used in the present methods. Such solid supports are envisioned to be removable with organic solvents for example, allowing for subsequent rehydration of preserved tissue.

RNA is extracted from the FPE cells by any of the methods as described in U.S. patent application Ser. No. 09/469,338, filed Dec. 20, 1999, now U.S. Pat. No. 6,248,535, which is hereby incorporated by reference in its entirety. Fixed and paraffin-embedded (FPE) tissue samples as described herein refers to storable or archival tissue samples. RNA may be isolated from an archival pathological sample or biopsy sample which is first deparaffinized. An exemplary deparaffinization method involves washing the paraffinized sample with an organic solvent, such as xylene, for example. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration, for example. Alternatively, the sample is simultaneously deparaffinized and rehydrated. RNA is then extracted from the sample.

For RNA extraction, the fixed or fixed and deparaffinized samples can be homogenized using mechanical, sonic or other means of homogenization. Rehydrated samples may be homogenized in a solution comprising a chaotropic agent, such as guanidinium thiocyanate (also sold as guanidinium isothiocyanate). Homogenized samples are heated to a temperature in the range of about 50 to about 100° C. in a chaotropic solution, which contains an effective amount of a chaotropic agent, such as a guanidinium compound. A preferred chaotropic agent is guanidinium thiocyanate.

An "effective concentration of chaotropic agent" is chosen such that at an RNA is purified from a paraffin-embedded sample in an amount of greater than about 10-fold that isolated in the absence of a chaotropic agent. Chaotropic agents include: guanidinium compounds, urea, formamide, potassium iodiode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5 M with a preferred value of about 4 M. If RNA is already in solution, the guanidinium solution may be of higher concentration such that the final concentration achieved in the sample is in the range of about 1 to about 5 M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and β-mercaptoethanol (BME). The chaotropic solution may also contain RNAse inhibitors.

Homogenized samples may be heated to a temperature in the range of about 50 to about 100° C. in a chaotropic solution, which contains an effective amount of a chaotropic agent, such as a guanidinium compound. A preferred chaotropic agent is guanidinium thiocyanate.

RNA is then recovered from the solution by, for example, phenol chloroform extraction, ion exchange chromatography or size-exclusion chromatography. RNA may then be further purified using the techniques of extraction, electrophoresis, chromatography, precipitation or other suitable techniques.

The quantification of GST-pi mRNA from purified total mRNA from fresh, frozen or fixed is preferably carried out using reverse-transcriptase polymerase chain reaction (RT-PCR) methods common in the art, for example. Other methods of quantifying of GST-pi mRNA include for example, the use of molecular beacons and other labeled probes useful in multiplex PCR. Additionally, the present invention envisages the quantification of GST-pi mRNA via use of PCR-free systems employing, for example fluorescent labeled probes similar to those of the Invader® Assay (Third Wave Technologies, Inc.). Most preferably, quantification of GST-pi cDNA and an internal control or house keeping gene (e.g. β-actin) is done using a fluorescence based real-time detection method (ABI PRISM 7700 or 7900 Sequence Detection System [TaqMan®], Applied Biosystems, Foster City, Calif.) or similar system as described by Heid et al., (Genome Res 1996;6:986–994) and Gibson et al.(Genome Res 1996;6:995–1001). The output of the ABI 7700 (TaqMan® Instrument) is expressed in Ct's or "cycle thresholds". With the TaqMan® system, a highly expressed gene having a higher number of target molecules in a sample generates a signal with fewer PCR cycles (lower Ct) than a gene of lower relative expression with fewer target molecules (higher Ct).

As used herein, a "house keeping" gene or "internal control" is meant to include any constitutively or globally expressed gene whose presence enables an assessment of GST-pi mRNA levels. Such an assessment comprises a determination of the overall constitutive level of gene transcription and a control for variations in RNA recovery. "House-keeping" genes or "internal controls" can include, but are not limited to the cyclophilin gene, β-actin gene, the transferrin receptor gene, GAPDH gene, and the like. Most preferably, the internal control gene is β-actin gene as described by Eads et al., Cancer Research 1999; 59:2302–2306.

A control for variations in RNA recovery requires the use of "calibrator RNA." The "calibrator RNA" is intended to be any available source of accurately pre-quantified control RNA. Preferably, Adult Colon, Disease Human Total RNA, (Cat. No. #735263) from Stratagene, is used.

"Uncorrected Gene Expression (UGE)" as used herein refers to the numeric output of GST-pi expression relative to an internal control gene generated by the TaqMan® instrument. The equation used to determine UGE is shown in Example 3, and illustrated with sample calculations in FIG. 4.

A further aspect of this invention provides a method to normalize uncorrected gene expression (UGE) values acquired from the TaqMan® instrument with "known relative gene expression" values derived from non-TaqMan® technology. Preferably, the known non-TaqMan® derived relative GST-pi: β-actin expression values are normalized with TaqMan® derived GST-pi UGE values from a tissue sample.

"Corrected Relative GST-pi Expression" as used herein refers to normalized GST-pi expression whereby UGE is multiplied with a GST-pi specific correction factor ($K_{GST-pi}$), resulting in a value that can be compared to a known range of GST-pi expression levels relative to an internal control gene. Example 3 and FIG. 4 illustrate these calculations in detail. These numerical values allow the determination of whether or not the "Corrected Relative GST-pi Expression" of a particular sample falls above or below the "predetermined threshold" level. The predetermined threshold level of Corrected Relative GST-pi Expression to β-actin level is about $1.0 \times 10^{-3}$. $K_{GST-pi}$ specific for GST-pi, the internal control β-actin and calibrator Adult Colon, Disease Human Total RNA, (Cat. No. #735263) from Stratagene, is $7.28 \times 10^{-3}$.

"Known relative gene expression" values are derived from previously analyzed tissue samples and are based on the ratio of the RT-PCR signal of a target gene to a constitutively expressed internal control gene (e.g. β-Actin, GAPDH, etc.). Preferably such tissue samples are formalin fixed and paraffin-embedded (FPE) samples and RNA is extracted from them according to the protocol described in Example 1 and in U.S. patent application Ser. No. 09/469,338, filed Dec. 20, 1999, now U.S. Pat. No. 6,248,535, which is hereby incorporated by reference in its entirety. To quantify gene expression relative to an internal control standard quantitative RT-PCR technology known in the art is used. Pre-TaqMan® technology PCR reactions are run for a fixed number of cycles (i.e., 30) and endpoint values are reported for each sample. These values are then reported as a ratio of GST-pi expression to β-actin expression. See U.S. Pat. No. 5,705,336 to Reed et al.

$K_{GST-pi}$ may be determined for an internal control gene other than β-actin and/or a calibrator RNA different than Adult Colon, Disease Human Total RNA, (Cat. No. #735263) from Stratagene. To do so, one must calibrate both the internal control gene and the calibrator RNA to tissue samples for which GST-pi expression levels relative to that particular internal control gene have already been determined (i.e., "known relative gene expression"). Preferably such tissue samples are formalin fixed and paraffin-embedded (FPE) samples and RNA is extracted from them according to the protocol described in Example 1 and in U.S. patent application Ser. No. 09/469,338, filed Dec. 20, 1999, now U.S. Pat. No. 6,248,535, which is hereby incorporated by reference in its entirety. Such a determination can be made using standard pre-TaqMan®, quantitative RT-PCR techniques well known in the art. Upon such a determination, such samples have "known relative gene expression" levels of GST-pi useful in the determining a new $K_{GST-pi}$ specific for the new internal control and/or calibrator RNA as described in Example 3.

The methods of the invention are applicable to a wide range of tissue and tumor types and so can be used for assessment of clinical treatment of a patient and as a diagnostic or prognostic tool for a range of cancers including breast, head and neck, lung, esophageal, colorectal, and others. In a preferred embodiment, the present methods are applied to prognosis of esophagocardiac adenocarcinoma.

Pre-chemotherapy treatment tumor biopsies are usually available only as fixed paraffin embedded (FPE) tissues, generally containing only a very small amount of heterogeneous tissue. Such FPE samples are readily amenable to microdissection, so that GST-pi gene expression may be determined in tumor tissue uncontaminated with stromal tissue. Additionally, comparisons can be made between stromal and tumor tissue within a biopsy tissue sample, since such samples often contain both types of tissues.

Generally, any oligonucleotide pair that flanks a region of GST-pi gene may be used to carry out the methods of the invention. Primers hybridizing under stringent conditions to a region of the GST-pi gene for use in the present invention will amplify a product between 20–1000 base pairs, preferably 50–100 base pairs, most preferably less than 100 base pairs.

The invention provides specific oligonucleotide primers pairs and oligonucleotide primers substantially identical thereto, that allow particularly accurate assessment of GST-pi expression in FPE tissues. Preferable are oligonucleotide primers, GST-F (SEQ ID NO: 1) and GST-R (SEQ ID NO: 2), (also referred to herein as the oligonucleotide primer pair GST) and oligonucleotide primers substantially identical thereto. The oliogonucleotide primers GST-F (SEQ ID NO: 1) and GST-R, (SEQ ID NO: 2) have been shown to be particularly effective for measuring GST-pi mRNA levels using RNA extracted from the FPE cells by any of the methods for mRNA isolation, for example as described Example 1 and in U.S. patent application Ser. No. 09/469,338, filed Dec. 20, 1999, now U.S. Pat. No. 6,248,535, which is hereby incorporated by reference in its entirety.

"Substantially identical" in the nucleic acid context as used herein, means hybridization to a target under stringent conditions, and also that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95–98% of the nucleotides. Selective hybridization exists when the hybridization is more selective than total lack of specificity. See, Kanehisa, Nucleic Acids Res., 12:203–213 (1984).

This invention includes substantially identical oligonucleotides that hybridize under stringent conditions (as defined herein) to all or a portion of the oligonucleotide primer sequence of GST-F (SEQ ID NO: 1), its complement or GST-R (SEQ ID NO: 2), or its complement.

Under stringent hybridization conditions, only highly complementary, i.e., substantially similar nucleic acid sequences hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The hybridizing portion of the nucleic acids is typically at least 10 (e.g., 15) nucleotides in length. The hybridizing portion of the hybridizing nucleic acid is at least about 80%, preferably at least about 95%, or most preferably about at least 98%, identical to the sequence of a portion or all of oligonucleotide primer GST-F (SEQ ID NO: 1), its complement or GST-R (SEQ ID NO: 2), or its complement.

Hybridization of the oligonucleotide primer to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5×Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

Oligonucleotide primers disclosed herein are capable of allowing accurate assessment of GST-pi gene expression in a fixed or fixed and paraffin embedded tissue, as well as frozen or fresh tissue. This is despite the fact that RNA derived from FPE samples is more fragmented relative to that of fresh or frozen tissue. Thus, the methods of the invention are suitable for use in assaying GST-pi expression levels in FPE tissue where previously there existed no way to assay GST-pi gene expression using fixed tissues.

From the measurement of the amount of GST-pi mRNA that is expressed in the tumor, the skilled practitioner can make a prognosis concerning clinical resistance of a tumor to a particular genotoxin, preferably a platinum-based chemotherapy, or to a chemotherapy inducing a similar type of DNA damage. Platinum-based chemotherapies cause a "bulky adduct" of the DNA, wherein the primary effect is to distort the three-dimensional conformation of the double helix. Such compounds are meant to be administered alone, or together with other chemotherapies such as gemcitabine (Gem) or 5-Fluorouracil (5-FU).

Many compounds are commonly given with platinum-based chemotherapy agents. For example, BEP (bleomycin, etoposide, cisplatin) is used for testicular cancer, MVAC (methotrexate, vinblastine, doxorubicin, cisplatin) is used for bladder cancer, MVP (mitomycin C, vinblastine, cisplatin) is used for non-small cell lung cancer treatment. Many studies have documented interactions between platinum-containing agents. Therapeutic drug synergism, for example, has been reported for many drugs potentially included in a platinum based chemotherapy. A very short list of recent references for this include the following: Okamoto et al., Urology 2001; 57:188–192.; Tanaka et al., Anticancer Research 2001; 21:313–315; Slamon et al., Seminars in Oncology 2001; 28:13–19; Lidor et al., Journal of Clinical Investigation 1993; 92:2440–2447; Leopold et al., NCI Monographs 1987;99–104; Ohta et al., Cancer Letters 2001; 162:39–48; van Moorsel et al., British Journal of Cancer 1999; 80:981–990.

Platinum-based genotoxic chemotherapies comprises heavy metal coordination compounds which form covalent DNA adducts. Generally, these heavy metal compounds bind covalently to DNA to form, in pertinent part, cis-1,2-intrastrand dinucleotide adducts. Generally, this class is represented by cis-diamminedichloroplatinum (II) (cisplatin), and includes cis-diammine-(1,1-cyclobutanedicarboxylato) platinum(II) (carboplatin), cis-diammino-(1,2-cyclohexyl) dichloroplatinum(II), and cis-(1,2-ethylenediammine) dichloroplatinum(II). Platinum first agents include analogs or derivatives of any of the foregoing representative compounds.

Tumors currently manageable by platinum coordination compounds include testicular, endometrial, cervical, gastric, squamous cell, adrenocortical and small cell lung carcinomas along with medulloblastomas and neuroblastomas. Trans-Diamminedichloroplatinum (II) (trans-DDP) is clinically useless owing, it is thought, to the rapid repair of its DNA adducts. The use of trans-DDP as a chemotherapeutic agent herein likely would provide a compound with low toxicity in nonselected cells, and high relative toxicity in selected cells. In a preferred embodiment, the platinum compound is cisplatin.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

RNA Isolation from FPE Tissue

RNA is extracted from paraffin-embedded tissue by the following general procedure.

A. Deparaffinization and Hydration of Sections:

(1) A portion of an approximately 10 μM section is placed in a 1.5 mL plastic centrifuge tube.

(2) 600 μL, of xylene are added and the mixture is shaken vigorously for about 10 minutes at room temperature (roughly 20 to 25° C.).

(3) The sample is centrifuged for about 7 minutes at room temperature at the maximum speed of the bench top centrifuge (about 10–20,000×g).

(4) Steps 2 and 3 are repeated until the majority of paraffin has been dissolved. Two or more times are normally required depending on the amount of paraffin included in the original sample portion.

(5) The xylene solution is removed by vigorously shaking with a lower alcohol, preferably with 100% ethanol (about 600 μL) for about 3 minutes.

(6) The tube is centrifuged for about 7 minutes as in step (3). The supernatant is decanted and discarded. The pellet becomes white.

(7) Steps 5 and 6 are repeated with successively more dilute ethanol solutions: first with about 95% ethanol, then with about 80% and finally with about 70% ethanol.

(8) The sample is centrifuged for 7 minutes at room temperature as in step (3). The supernatant is discarded and the pellet is allowed to dry at room temperature for about 5 minutes.

B. RNA Isolation with Phenol-Chloroform (1) 400 μL guanidine isothiocyanate solution including 0.5% sarcosine and 8 μL dithiothreitol is added.

(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).

(3) The sample is then heated at about 95° C. for about 5–20 minutes. It is preferable to pierce the cap of the tube containing the sample with a fine gauge needle before heating to 95° C. Alternatively, the cap may be affixed with a plastic clamp or with laboratory film.

(4) The sample is then extracted with 50 μL 2 M sodium acetate at pH 4.0 and 600 μL of phenol/chloroform/isoamyl alcohol (10:1.93:0.036), prepared fresh by mixing 18 mL phenol with 3.6 mL of a 1:49 isoamyl alcohol:chloroform solution. The solution is shaken vigorously for about 10 seconds then cooled on ice for about 15 minutes.

(5) The solution is centrifuged for about 7 minutes at maximum speed. The upper (aqueous) phase is transferred to a new tube.

(6) The RNA is precipitated with about 10 μL glycogen and with 400 μL isopropanol for 30 minutes at −20° C.

(7) The RNA is pelleted by centrifugation for about 7 minutes in a benchtop centrifuge at maximum speed; the supernatant is decanted and discarded; and the pellet washed with approximately 500 μL of about 70 to 75% ethanol.

(8) The sample is centrifuged again for 7 minutes at maximum speed. The supernatant is decanted and the pellet air dried. The pellet is then dissolved in an appropriate buffer for further experiments (e.g., 50 pI. 5 mM Tris chloride, pH 8.0).

Example 2 mRNA Reverse Transcription and PCR

Reverse Transcription: RNA was isolated from microdissected or non-microdissected formalin fixed paraffin embedded (FPE) tissue as illustrated in Example 1 and as previously described in U.S. application Ser. No. 09/469,338 filed Dec. 20, 1999, now U.S. Pat. No. 6,248,535, which is hereby incorporated by reference in its entirety. After precipitation with ethanol and centrifugation, the RNA pellet was dissolved in 50 μl of 5 mM Tris/Cl at pH 8.0. M-MLV Reverse Transcriptase will extend an oligonucleotide primer hybridized to a single-stranded RNA or DNA template in the presence of deoxynucleotides, producing a complementary strand. The resulting RNA was reverse transcribed with random hexamers and M-MLV Reverse Transcriptase from Life Technologies. The reverse transcription was accomplished by mixing 25 μl of the RNA solution with 25.5 μl of "reverse transcription mix" (see below). The reaction was placed in a thermocycler for 8 min at 26° C. (for binding the random hexamers to RNA), 45 min at 42° C. (for the M-MLV reverse transcription enzymatic reaction) and 5 min at 95° C. (for heat inactivation of DNAse).

"Reverse transcription mix" consists of 10 ul 5×buffer (250 mM Tris-HCl, pH 8.3, 375 mM KCl, 15 mM MgCl2), 0.5 ul random hexamers (50 O.D. dissolved in 550 ul of 10 mM Tris-HCl pH 7.5) 5 ul 10 mM dNTPs (dATP, dGTP, dCTP and dTTP), 5 ul 0.1 M DTT, 1.25 ul BSA (3 mg/ml in 10 mM Tris-HCL, pH 7.5), 1.25 ul RNA Guard 24,800 U/ml (RNAse inhibitor) (Porcine #27-0816, Amersham Pharmacia) and 2.5 ul MMLV 200 U/ul (Life Tech Cat #28025-02).

Final concentrations of reaction components are: 50 mM Tris-HCl, pH 8.3, 75 mM KCl, 3 mM MgCl2, 1.0 mM dNTP, 1.0 mM DTT, 0.00375. mg/ml BSA, 0.62 U/ul RNA Guard and 10 U/ul MMLV.

PCR Quantification of mRNA expression. Quantification of GST-pi cDNA and an internal control or house keeping gene (e.g., β-actin) cDNA was done using a fluorescence based real-time detection method (ABI PRISM 7700 or 7900 Sequence Detection System [TaqMan®], Applied Biosystems, Foster City, Calif.) as described by Heid et al., (Genome Res 1996;6:986–994); Gibson et al., (Genome Res 1996;6:995–1001). In brief, this method uses a dual labelled fluorogenic TaqMan® oligonucleotide probe, (GST-219T (SEQ ID NO: 3), $T_m$=69° C.), that anneals specifically within the forward and reverse primers. Laser stimulation within the capped wells containing the reaction mixture causes emission of a 3' quencher dye (TAMRA) until the probe is cleaved by the 5' to 3' nuclease activity of the DNA polymerase during PCR extension, causing release of a 5' reporter dye (6FAM). Production of an amplicon thus causes emission of a fluorescent signal that is detected by the TaqMan®'s CCD (charge-coupled device) detection camera, and the amount of signal produced at a threshold cycle within the purely exponential phase of the PCR reaction reflects the starting copy number of the sequence of interest. Comparison of the starting copy number of the sequence of interest with the starting copy number of the internal control gene provides a relative gene expression level. TaqMan® analyses yield values that are expressed as ratios between two absolute measurements (gene of interest/internal control gene).

The PCR reaction mixture consisted 0.5 μl of the reverse transcription reaction containing the cDNA prepared as described above 600 nM of each oligonucleotide primer (GST-F (SEQ ID NO:1), $T_m$=59° C. and GST-R (SEQ ID NO: 2), $T_m$=59° C.), 200 nM TaqMan® probe (SEQ ID NO:3), 5 U AmpliTaq Gold Polymerase, 200 μM each DATP, dCTP, dGTP, 400 μM dTTP, 5.5 mM MgCl$_2$, and 1×TaqMan® Buffer A containing a reference dye, to a final volume of less than or equal to 25 μl (all reagents Applied Biosystems, Foster City, Calif). Cycling conditions were, 95° C. for 10 min, followed by 45 cycles at 95° C. for 15 s and 60° C. for 1 min. Oligonucleotides used to quantify internal control gene β-Actin were β-Actin TaqMan® probe (SEQ ID NO: 4), β-Actin-592F (SEQ ID NO: 5) and β-Actin-651R (SEQ ID NO: 6).

The oligonucleotide primers GST-F (SEQ ID NO:1) and GST-R (SEQ ID NO: 2), used in the above described reaction will amplify a 72 bp product.

Example 3

Determining the Uncorrected Gene Expression (UGE) for GST-pi

Two pairs of parallel reactions are carried out, i.e., "test" reactions and the "calibration" reactions. The GST-pi amplification reaction and the β-actin internal control amplification reaction are the test reactions. Separate GST-pi and β-actin amplification reactions are performed on the calibrator RNA template and are referred to as the calibration reactions. The TaqMan® instrument will yield four different cycle threshold (Ct) values: $Ct_{GST-pi}$ and $Ct_{\beta-actin}$ from the test reactions and $Ct_{GST-pi}$ and $Ct_{\beta-actin}$ from the calibration reactions. The differences in Ct values for the two reactions are determined according to the following equation:

$$\Delta Ct_{test}=Ct_{GST-pi}-Ct_{\beta-actin} \text{(From the ``test'' reaction)}$$

$$\Delta Ct_{calibrator}=Ct_{GST-pi}-Ct_{\beta actin} \text{(From the ``calibration'' reaction)}$$

Next the step involves raising the number 2 to the negative ΔCt, according to the following equations.

$$2^{-\Delta Ct}{}_{test} \text{(From the ``test'' reaction)}$$

$$2^{-\Delta Ct}{}_{calibrator} \text{(From the ``calibration'' reaction)}$$

In order to then obtain an uncorrected gene expression for GST-pi from the TaqMan® instrument the following calculation is carried out:

Uncorrected gene expression (UGE) for GST-pi=
$$2^{-\Delta Ct}{}_{test}/2^{-\Delta Ct}{}_{calibrator}$$

Normalizing UGE with Known Relative GST-pi Expression Levels

The normalization calculation entails a multiplication of the UGE with a correction factor ($K_{GST-pi}$) specific to GST-pi and a particular calibrator RNA. A correction factor $K_{GST-pi}$ can also be determined for any internal control gene and any accurately pre-quantified calibrator RNA. Preferably, the internal control gene β-actin and the accurately pre-quantified calibrator Adult Colon, Disease Human Total RNA, (Cat. No. #735263) from Stratagene, are used. Given these reagents correction factor $K_{GST-pi}$ equals $7.28 \times 10^{-3}$.

Normalization is accomplished using a modification of the ΔCt method described by Applied Biosystems, the TaqMan® manufacturer, in User Bulletin #2 and described above. To carry out this procedure, the UGE of 6 different test tissues was analyzed for GST-pi expression using the TaqMan® methodology described above. The internal control gene β-actin and the calibrator RNA, Adult Colon, Disease Human Total RNA, (Cat. No. #735263) from Stratagene was used.

The known relative GST-pi expression level of each sample 14-1, 14-5, 14-8, 13-24, 13-25 was divided by its corresponding TaqMan® derived UGE to yield an unaveraged correction factor K.

$$K_{unaveraged}=\text{Known Values}/UGE$$

Next, all of the K values are averaged to determine a single $K_{GST-pi}$ correction factor specific for GST-pi, Adult Colon, Disease Human Total RNA, (Cat. No. #735263) from Stratagene from calibrator RNA and β-actin.

Therefore, to determine the Corrected Relative GST-pi Expression in an unknown tissue sample on a scale that is consistent with pre-TaqMan® GST-pi expression studies, one merely multiplies the uncorrected gene expression data (UGE) derived from the TaqMan® apparatus with the $K_{GST-pi}$ specific correction factor, given the use of the same internal control gene and calibrator RNA.

Corrected Relative GST-pi Expression=$UGE \times K_{GST-pi}$

A $K_{GST-pi}$ may be determined using any accurately pre-quantified calibrator RNA or internal control gene. Future sources of accurately pre-quantified RNA can be calibrated to samples with known relative GST-pi expression levels as described in the method above or may now be calibrated against a previously calibrated calibrator RNA such as Adult Colon, Disease Human Total RNA, (Cat. No. #735263) from Stratagene described above.

For example, if a subsequent $K_{GST-pi}$ is determined for a different internal control gene and/or a different calibrator RNA, one must calibrate both the internal control gene and the calibrator RNA to tissue samples for which GST-pi expression levels relative to that particular internal control gene have already been determined. Such a determination can be made using standard pre-TaqMan®, quantitative RT-PCR techniques well known in the art. The known expression levels for these samples will be divided by their corresponding UGE levels to determine a K for that sample. K values are then averaged depending on the number of known samples to determine a new $K_{GST-pi}$ specific to the different internal control gene and/or calibrator RNA.

Example 4

GST-pi Expression Correlates with Survivability

Total mRNA was isolated from microdissected FPE pretreatment tumor samples, and Corrected Relative GST-pi Expression was measured using quantitative RT-PCR as described in Examples 2 and 3. A method for mRNA isolation from such samples is described in Example 1 and in U.S. patent application Ser. No. 09/469,338, filed Dec. 20, 1999, now U.S. Pat. No. 6,248,535, and is hereby incorporated by reference in its entirety.

The values of the gene expressions were correlated with clinical outcome using appropriate statistical methods. Survival was estimated according to Kaplan and Meier (Kaplan et al., J Am Stat Assoc 1958; 53: 187–220). Univariate analysis was performed with the log-rank test (Mantel, Chemother Rep 1966; 50: 163–170). The level of significance was set to P<0.05. All P values reported were based on two-sided tests.

A total of 31 esophageal or gastroesophageal junction (esophagocardiac) adenocarcinoma tumor specimens from 31 patients were analysed for GST-pi mRNA expression analysis. Thirty (97%) of the patients were male, the median age was 64 years (mean 60.9 years, range 36–78 years). The ethnic background of this group included 29 Caucasians, 1 Asian, and 1 African-American. Using TNM clinical staging criteria, 2 (6.5%) of the patients had Stage I disease, 22 (71%) had Stage II disease, 1 (3.2%) had Stage III disease, and 6 (19.4%) patients had Stage IV disease. Overall survival was assessable for all patients. The median overall survival was 17.17 months (mean 24.8 months, range 3.8–156.7 months). Twelve (38.7%) of the patients had died and 19 (61.3%) were alive.

The treatment consisted of all patients receiving two cycles of 5-FU given as 800 mg/m$^2$ per day for 5 days or 1000 mg/m$^2$ per day for 4 days plus 75 mg/m$^2$ cisplatin with concurrent 45 Gy radiation, followed by operative resection. For entry into the study, each patient had to have completed the chemotherapy regimen and the prescribed radiotherapy, undergone a gross complete resection, and lived at least 30 days after surgery.

Figure 2:
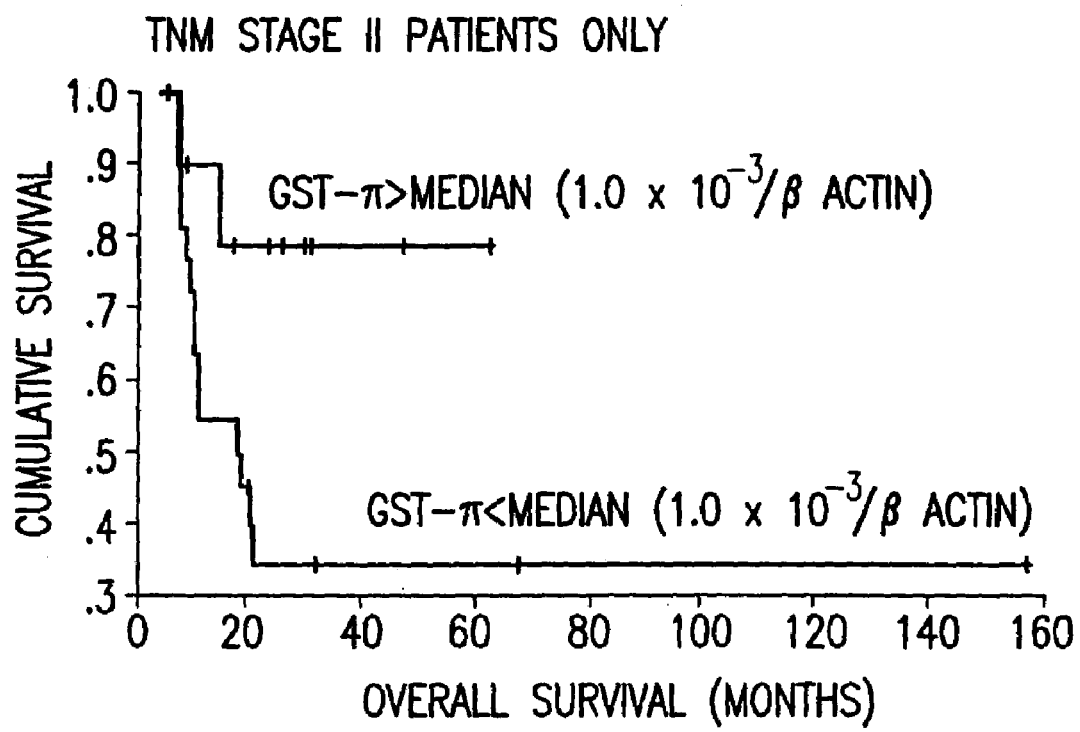
FIG. 2 is a graph showing survival analysis confined to patients with TNM Stage II esophagocardiac adenocarcinoma
Figure 3:
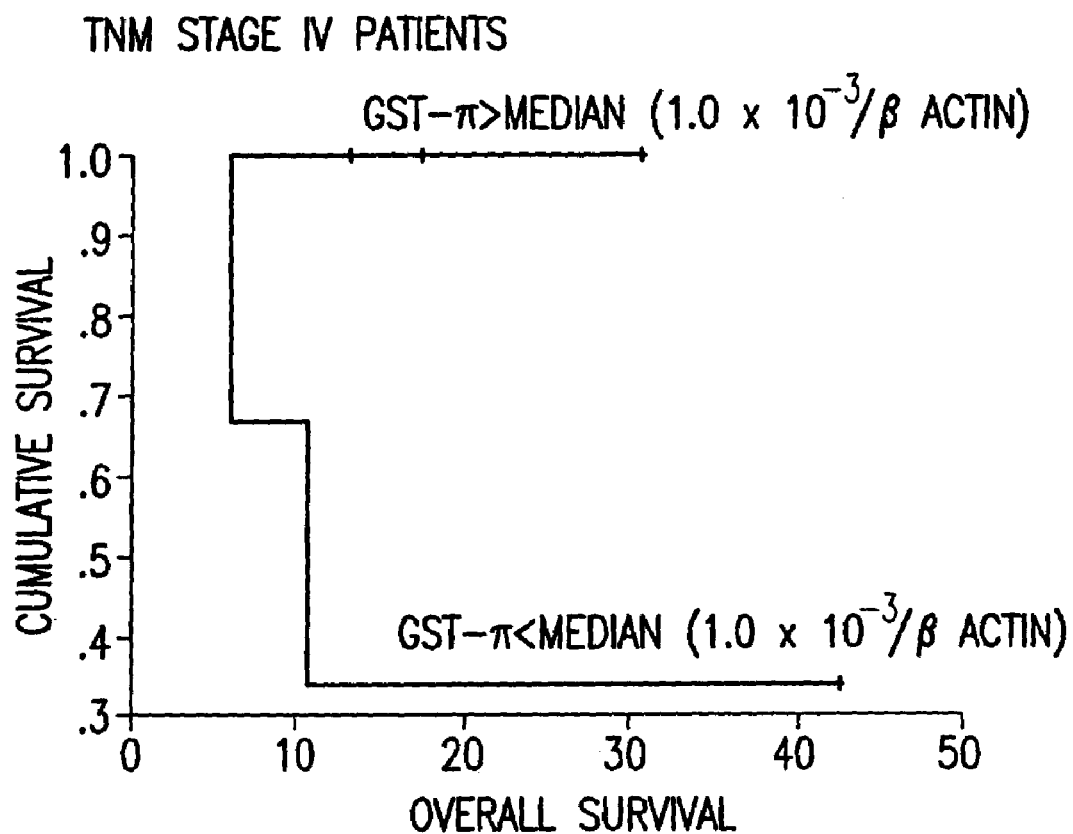
FIG. 3 is a graph showing survival analysis confined to patients with Stage IV esophagocardiac adenocarcinoma

The influence of tumor stage was accounted for by pooling the data over the TNM stage strata. Survival curves and log-rank statistics were generated for Stage II and Stage IV disease patients only because of the very small numbers of patients in the other stages. The median corrected relative GST-pi mRNA expression level was $1.0 \times 10^{-3}$ (mean $0.51 \times 10^{-3}$, range $0.0$–$16.1 \times 10^{-3}$, all values GST-pi$\times 10^{-3}$/β-actin). An analysis of survival according to GST-pi values showed that patients whose tumors had a relative GST-pi gene expression level higher than the median value had a statistically significant survival benefit compared to those with levels below the median value (P=0.0073, log-rank test). Accordingly, the median corrected relative GST-pi mRNA was assigned to be a threshold value. This association is shown graphically in FIG. 1. The relationship was independent of stage. FIGS. 2 and 3 show that the association was present if the analysis was confined only to those with Stage II or Stage IV disease.

GST-pi mRNA expression is a significant prognostic factor for patients with esophagocardiac adenocarcinoma who are treated with a cisplatin-containing regimen.

What is claimed is:

1. An oligonucleotide primer having the sequence of SEQ ID NO:1, wherein said primer is capable of amplifying a portion of GST-pi mRNA isolated from fixed and paraffin embedded (FPE) tumor tissue when used with SEQ ID NO: 2.

2. An oligonucleotide primer having the sequence of SEQ ID NO:2, wherein said primer is capable of amplifying a portion of GST-pi mRNA isolated from fixed and paraffin embedded (FPE) tumor tissue when used with SEQ ID NO: 1.

3. A kit for detecting expression of a GST-pi gene comprising the oligonucleotide primers of claim 1 and claim 2.

* * * * *